United States Patent
Bigolin et al.

(10) Patent No.: US 10,722,166 B2
(45) Date of Patent: Jul. 28, 2020

(54) METHOD AND SYSTEM FOR BIOMECHANICAL ANALYSIS OF THE POSTURE OF A CYCLIST AND AUTOMATIC CUSTOMIZED MANUFACTURE OF BICYCLE PARTS

(71) Applicant: ERGOVIEW S.R.L., Cesena (FO) (IT)

(72) Inventors: Giuseppe Bigolin, Rossano Veneto (IT); Luca Bartoli, Cesena (IT)

(*) Notice: Subject to any disclaimer, the term of this patent is extended or adjusted under 35 U.S.C. 154(b) by 413 days.

(21) Appl. No.: 15/531,457

(22) PCT Filed: Dec. 30, 2015

(86) PCT No.: PCT/IB2015/060050
§ 371 (c)(1),
(2) Date: May 29, 2017

(87) PCT Pub. No.: WO2016/108197
PCT Pub. Date: Jul. 7, 2016

(65) Prior Publication Data
US 2017/0332956 A1    Nov. 23, 2017

(30) Foreign Application Priority Data

Dec. 30, 2014    (IT) .............................. VI2014A0337

(51) Int. Cl.
*A61B 5/22*    (2006.01)
*A61B 5/11*    (2006.01)
(Continued)

(52) U.S. Cl.
CPC ............ *A61B 5/222* (2013.01); *A61B 5/0062* (2013.01); *A61B 5/0205* (2013.01); *A61B 5/107* (2013.01);
(Continued)

(58) Field of Classification Search
None
See application file for complete search history.

(56) References Cited

U.S. PATENT DOCUMENTS

| | | | |
|---|---|---|---|
| 6,423,015 B1* | 7/2002 | Winkenbach | A61B 5/1079 600/587 |
| 2007/0142177 A1* | 6/2007 | Simms | A61B 5/1127 482/8 |
| 2014/0379135 A1* | 12/2014 | Kristiansen | A63B 22/0046 700/275 |

FOREIGN PATENT DOCUMENTS

| | | |
|---|---|---|
| DE | 102008014713 | 9/2008 |
| EP | 2837329 | 2/2015 |

(Continued)

OTHER PUBLICATIONS

English translation of FR2974288A1, Google Patents, 5 pages. (Year: 2012).*

(Continued)

*Primary Examiner* — Suzanne Lo
(74) *Attorney, Agent, or Firm* — Themis Law

(57) ABSTRACT

A system for biomechanical analysis of user posture and automatic customized manufacture of bicycle parts includes a servo-assisted simulator having a handlebar, a saddle, pedal cranks, and actuators, a device detecting input data that includes a 3D scanner for automatically detecting the position of body segments of the user and the angular ranges therebetween and generating three-dimensional physical data units, an electronic platform detecting pressure data of the user, a pair of insoles detecting plantar pressure, a computer connected to the actuators and to the detection device, a memory unit storing optimized initial data and instantaneous data, software comparing the optimized initial data and the instantaneous data and generating final data of the characteristics of the main parts, a spatial representation (Continued)

device spatially representing the final data, and a device for immediate manufacture of the parts using 3D printers. A method of biomechanical analysis and custom manufacture of bicycle parts.

14 Claims, 10 Drawing Sheets

(51) Int. Cl.

| | |
|---|---|
| A61B 5/107 | (2006.01) |
| B62K 3/02 | (2006.01) |
| A61B 5/00 | (2006.01) |
| A61B 5/0205 | (2006.01) |
| A61B 5/103 | (2006.01) |
| B62J 1/00 | (2006.01) |
| B62K 21/12 | (2006.01) |
| B62M 3/08 | (2006.01) |
| G05B 19/4099 | (2006.01) |
| A61B 5/024 | (2006.01) |

(52) U.S. Cl.
CPC .......... *A61B 5/1036* (2013.01); *A61B 5/1077* (2013.01); *A61B 5/1079* (2013.01); *A61B 5/1114* (2013.01); *A61B 5/1116* (2013.01); *A61B 5/1121* (2013.01); *A61B 5/1128* (2013.01); *A61B 5/4884* (2013.01); *A61B 5/6807* (2013.01); *A61B 5/6895* (2013.01); *A61B 5/745* (2013.01); *B62J 1/007* (2013.01); *B62K 3/02* (2013.01); *B62K 21/12* (2013.01); *B62M 3/08* (2013.01); *G05B 19/4099* (2013.01); *A61B 5/02438* (2013.01); *A61B 2562/0247* (2013.01); *A61B 2576/00* (2013.01); *G05B 2219/49023* (2013.01)

(56) References Cited

FOREIGN PATENT DOCUMENTS

| | | | |
|---|---|---|---|
| FR | 2974288 A1 * | 10/2012 | ........... A61B 5/1072 |
| JP | S5932801 | 2/1984 | |
| WO | 20130186699 | 12/2013 | |

OTHER PUBLICATIONS

Hanna Watkin, "World's First Fully 3D Printed Readworlds-first-fully-3d-printed-road-racing-bike," Oct. 1, 2015 at all3dp.com/worlds-first-fully-3d-printed-road-racing-bike/ The whole document.

* cited by examiner

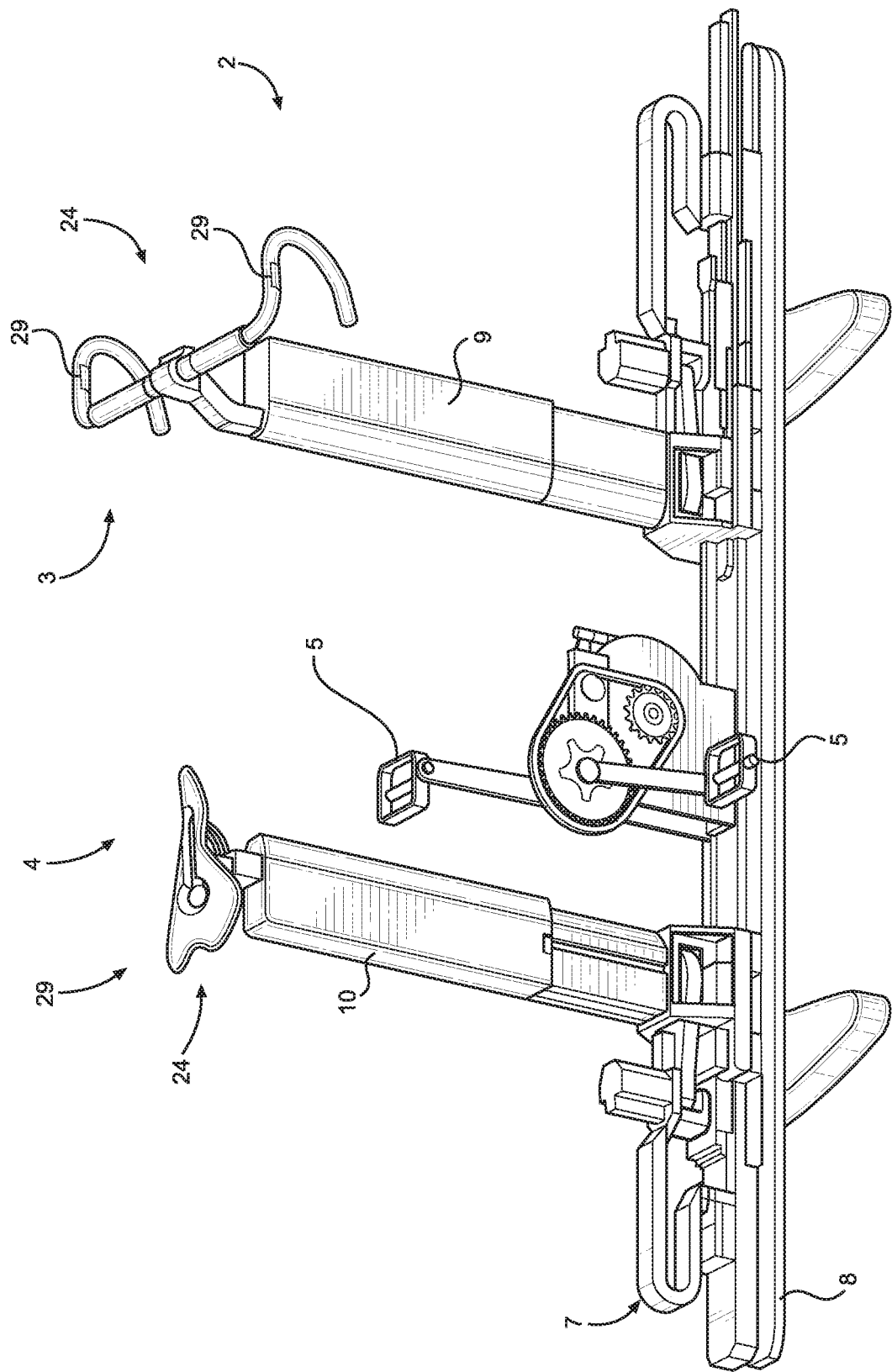

METHOD AND SYSTEM FOR BIOMECHANICAL ANALYSIS OF THE POSTURE OF A CYCLIST AND AUTOMATIC CUSTOMIZED MANUFACTURE OF BICYCLE PARTS

FIELD OF THE INVENTION

The present invention finds application in the field of sport equipments, and particularly relates to a method of biomechanical analysis of the posture of a user, and of automatic custom manufacture of bicycle parts.

The invention further relates to a system for carrying out such method.

BACKGROUND ART

It has been long known to be used methods and systems for biomechanical analysis of the posture of a cyclist according to his physical characteristics and the type of athletic or sports discipline he/she intends to practice.

With these methods, a user may select the bicycle frame that is most suitable to his/her characteristics, for automatic customized design of its parts, and may adjust the position of the saddle and the handlebar to optimize his/her posture during pedaling, in view of improving both riding comfort and performances.

US2007/0142177 discloses a system for determining and adjusting structural parameters of bicycles according to the postural characteristics of a user.

This prior art system uses a bicycle placed on a roller stand and a plurality of light-emitting indicators, preferably of LED type, which are designed to be placed on the body of the user and on the bicycle during the pedaling action, as well as a camera-type detector for capturing the light emitted by the indicators and to transmit it to a computer. Thus, the detector may record the change of relative position of the various light-emitting indication during exercise.

Software is installed in the computer for comparing the signals received by the detector with reference data stored in a database within the memory of the computer, to provide the optimized handlebar position relative to the ground, and to hence optimize the user's pedaling action.

A first drawback of this prior art system is that, when the position of certain joints of the user's body is detected by light-emitting indicators, the skeletal system can be only roughly approximated, and as a result the calculated position will not be really the best position for user's performances.

This is because the detector is a standard camera, which generates video frames to be later processed by the computer for generating anthropometric data of the user. These video devices are poorly sensitive and only allow reconstruction of numeric data associated with a substantially two-dimensional image, whereby relatively high dimensional error margins are introduced.

A further drawback of this prior art arrangement is that the light-emitting indicators shall be manually positioned by the operator on a user's body, and this increases the risk that they may be located in an inappropriate position with respect to the corresponding joint, thereby reducing measuring accuracy.

Yet another drawback of this prior art system is that certain anthropometric measurements of the user are performed manually, and are thus exposed to frequent errors and approximations. Furthermore, the parameters of the bicycle cannot be adjusted in real time, as the operator is required to stop angle detection to introduce angle values into the computerized system.

Another serious drawback is that the physical characteristics that are recorded at the start are only marginally considered for adjustment of bicycle parameters.

US2012/0323351 discloses a method of making bicycles of a given model with optimized parameters for a given user. The method comprises a first step in which certain physical characteristics of a user, including body weight and height, are acquired for pre-adjustment of the self-adaptive simulator that will be used for the pedaling test.

During exercise on the simulator, the angles of inclination of the pelvis and the knee of the user are recorded manually and later entered into a computer for generating the optimal position of the saddle and handlebar of a bicycle.

A further drawback of these known arrangements is that they allow optimization of bicycle parameters using a limited number of physical parameters of the user.

US2014/0379135 discloses a method and system for optical detection of a bicycle simulator having certain characteristics in common with the present invention.

In light of the above described prior art, one of the technical problems of the present invention may be deemed to be the need of providing a method and a system for biomechanical analysis of the posture of a user, that allows detection, analysis and processing of a plurality of physical data units of the user in an accurate, combined manner, for sizing, representing and providing the parts of a user-customized bicycle.

DISCLOSURE OF THE INVENTION

The general object of the present invention is to obviate the above drawbacks by solving the aforementioned technical problem.

A particular object of the present invention is to provide a method and a system for biomechanical analysis of the posture of a user that are highly efficient and relatively cost-effective.

A further object of the present invention is to provide a method and a system that can provide biomechanical analysis of the posture in an almost completely automatic manner.

A further object of the present invention is to provide a method and a system as mentioned hereinbefore that allow a user to adapt the parts of a bicycle to his/her own physical and anthropometric characteristics, while accounting for the stresses exerted by these parts on the user's body.

Yet another object of the present invention is to provide a method and a system of the above mentioned type that can reduce the overall times for biomechanical analysis of a user's posture.

These and other objects, as better explained hereafter, are fulfilled by a method of biomechanical analysis of the posture of a user as defined in claim 1.

These objects are also fulfilled by a system for biomechanical analysis of the posture of a user as defined in claim 7.

Advantageous embodiments of the invention are obtained in accordance with the dependent claims.

BRIEF DESCRIPTION OF THE DRAWINGS

Further features and advantages of the invention will be more apparent upon reading the detailed description of a preferred, non-exclusive embodiment of a method and a system for biomechanical analysis of the posture of a user and manufacture of bicycle parts according to the invention, which are described as a non-limiting example with the help of the annexed drawings, in which:

FIGS. 3A and 3B are a front perspective view and a rear perspective view of a first detail of the system of FIG. 1;

DETAILED DESCRIPTION OF A PREFERRED EMBODIMENT

Figure 1:
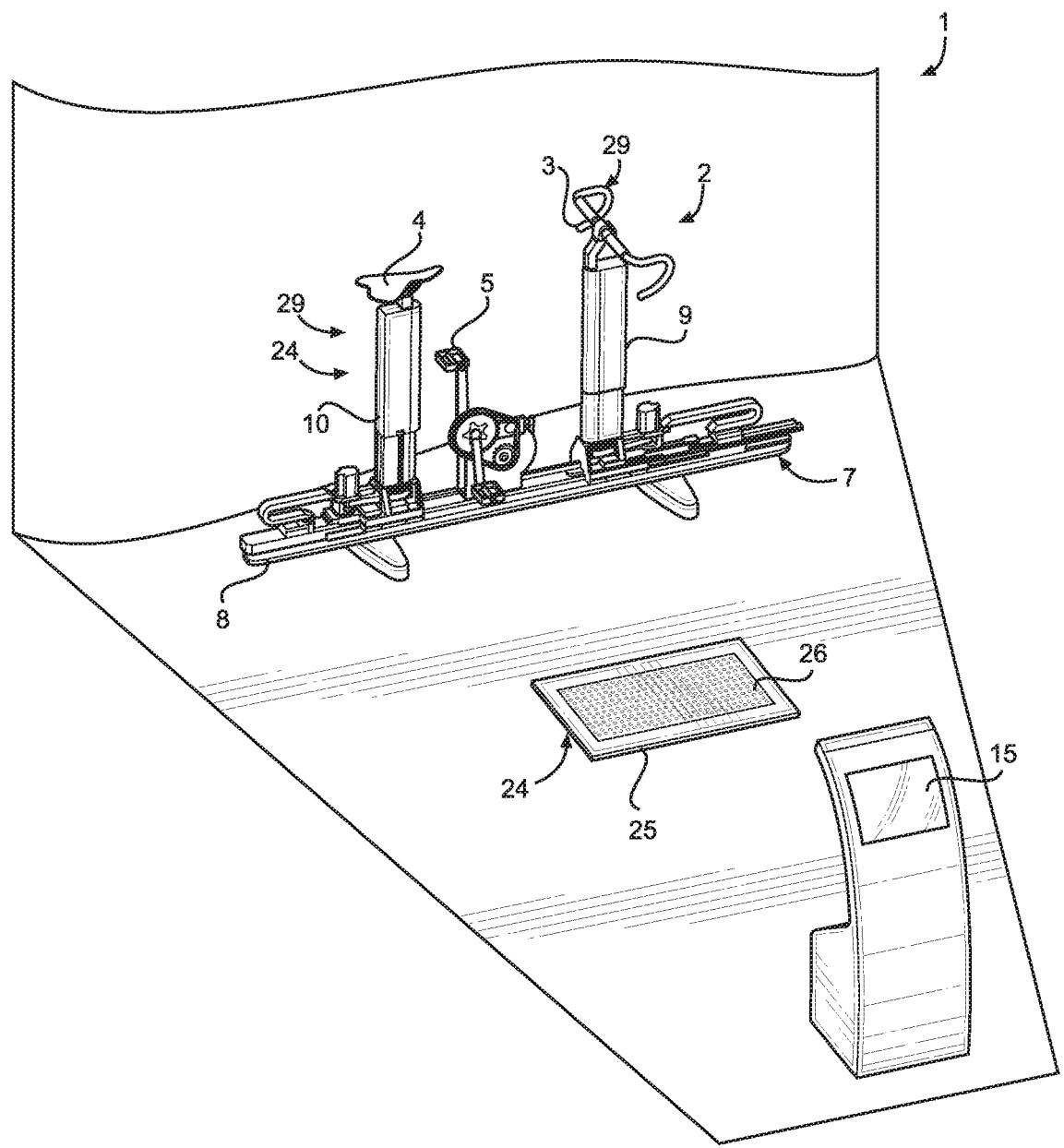
FIG. 1 is a front perspective view of a system for biomechanical analysis of the posture of a user according to the invention.

Referring to the above mentioned figures, there is shown a system or apparatus for biomechanical analysis of the posture of a user U and for manufacture of the parts of a bicycle, generally designated by numeral 1.

The system 1 of the invention is adapted to prepare the parts of a bicycle and adapt their sizes to fit a user U such that he/she may optimize his/her pedaling efficiency.

The biomechanical analysis system 1 as described herein is designed to be employed particularly but without limitation in specialized stores, sports centers, gyms, etc. for professionals.

In the embodiment as shown in the figures, the system 1 comprises a servo-assisted simulator 2 having a handlebar 3, a saddle 4 and a pair of pedal cranks 5, in addition to other details that are commonly found in bicycles, exercise bikes or other pedal-operated machines.

Figure 2:
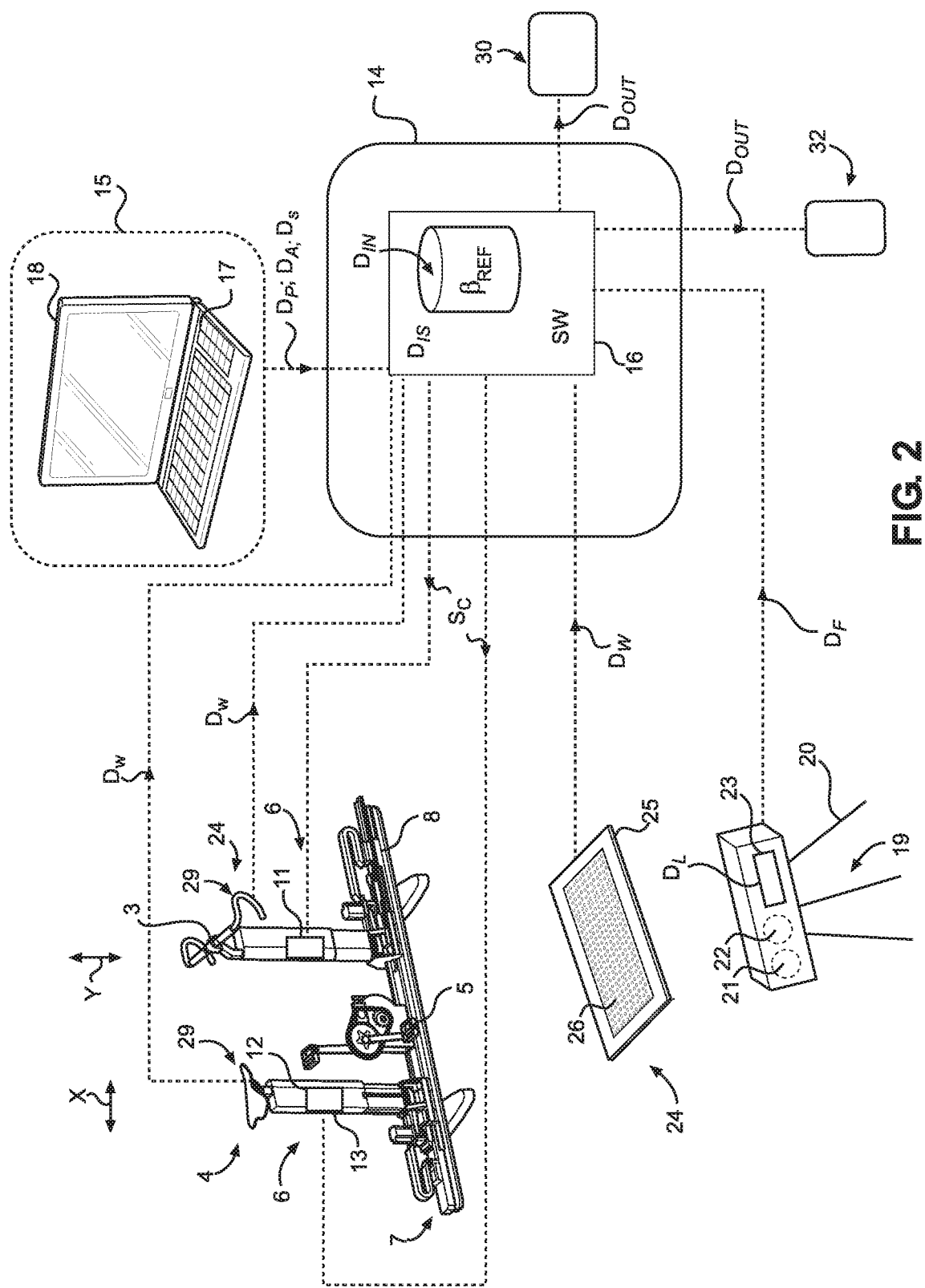
FIG. 2 is a schematic block diagram of the system of FIG. 1.

The servo-assisted simulator 2 is fitted with actuators 6, as shown in FIG. 2, for automatically adapting certain base parameters of the system 1 and changing the position of the handlebar 3, the saddle 4 and the pedal cranks 5.

Particularly, these base parameters may consist of at least the vertical position y of the handlebar 3 and the horizontal x and vertical y' positions of the saddle 4, for achieving the best position for the user U.

Figure 3B:
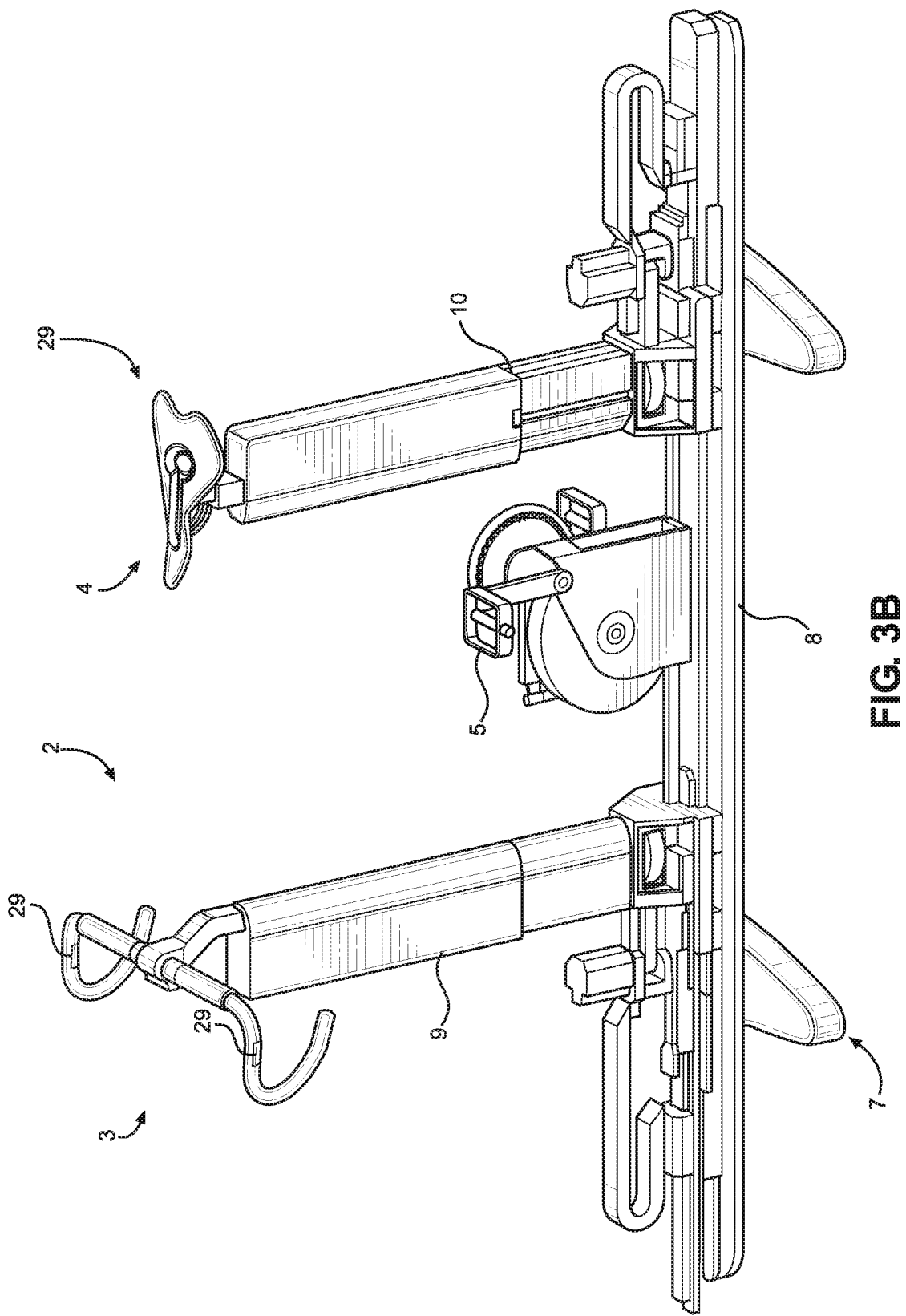

As shown in FIGS. 3A and 3B, the simulator comprises a ground-supported frame 7 having a substantially horizontal base 8 with a pair of vertical posts 9, 10 extending therefrom for supporting the saddle 4 and the handlebar 3.

At least one first actuator 11 operating on the handlebar 3 for changing its vertical position y and at least one second 12 and one third 13 actuators operating on the saddle 4 for adjusting its vertical y' and horizontal x positions respectively are fixed at the posts 9, 10.

The system 1 further comprises a computer 14 having interface means 15 for entering personal $D_P$ and historical $D_A$ input data of the user U as well as the desired type of physical activity $D_S$.

The computer 14 also comprises a memory unit 16 for storing optimized initial data $D_{IN}$ and instantaneous data $D_{IS}$ associated with the user U.

Particularly, the optimized initial data $D_{IN}$ includes the optimal angular ranges $\beta_{REF}$ of the body segments B of a general user U at his/her joints.

Preferably, the optimal angular ranges $\beta_{REF}$ can be retrieved from standard tables. For instance, a Caucasian male adult with no current or past diseases who practices road bicycle racing these reference angles have the following values:

Elbow angle: 170°;
Shoulder angle: 86°;
Lumbar spine angle: 140°;
Knee angle: 138°;
Ankle angle: 118°.

The interface means 15 may comprise an alphanumeric keyboard 17 and a digital display 18, possibly of touch screen type, for input and storage of certain personal $D_P$ and historical $D_A$ data of each user U.

The personal input data $D_P$ may include identity data, such as the name and gender of the user U, whereas the historical data $D_A$ may include information about any diseases he/she may have (had), and/or his/her current health conditions, such information being obviously given with the authorization of the person concerned and subject to confidentiality.

The operator may also use the interface means 15 to enter data $D_S$ concerning the type of cycling discipline that the user U intends to practice with the bicycle, such as road, track or mountain bike cycling, as well as exercise cycling, or the discipline and the required skill level.

The computer 14 may also be connected to the actuators 6 of the servo-assisted simulator 2 and be operably connected also to detection means 19 for acquiring anthropometric input data $D_L$ of the user U.

Preferably, the detection means 19 comprise a 3D scanner 20, which is connected to the computer and is adapted to automatically and directly detect the shape and three-dimensional position of the body C of the user U.

Preferably, as schematically shown in the diagram of FIG. 2, the scanner may comprise at least one RGB sensor 21 and at least one infrared IR sensor 22.

The combined operation of the RGB sensor 21 and the IR sensor 22 will cause the generation of anthropometric data $D_L$ from the space analyzed by the scanner 20 such that a highly-accurate digital reconstruction may be made therefrom.

Particularly, the scanner 20 can automatically detect the position of the body segments B of the user U and the angles β therebetween, to generate a plurality of three-dimensional physical data units $D_F$ of the user U.

Furthermore, the scanner 20 may be equipped with processor means 23, which are designed to process the three-dimensional physical data $D_F$ associated with the body C of the user U from the anthropometric data $D_L$ to thereby approximate the skeleton system of the user U by a plurality of body segments B joined together at the joints A.

Figure 4:
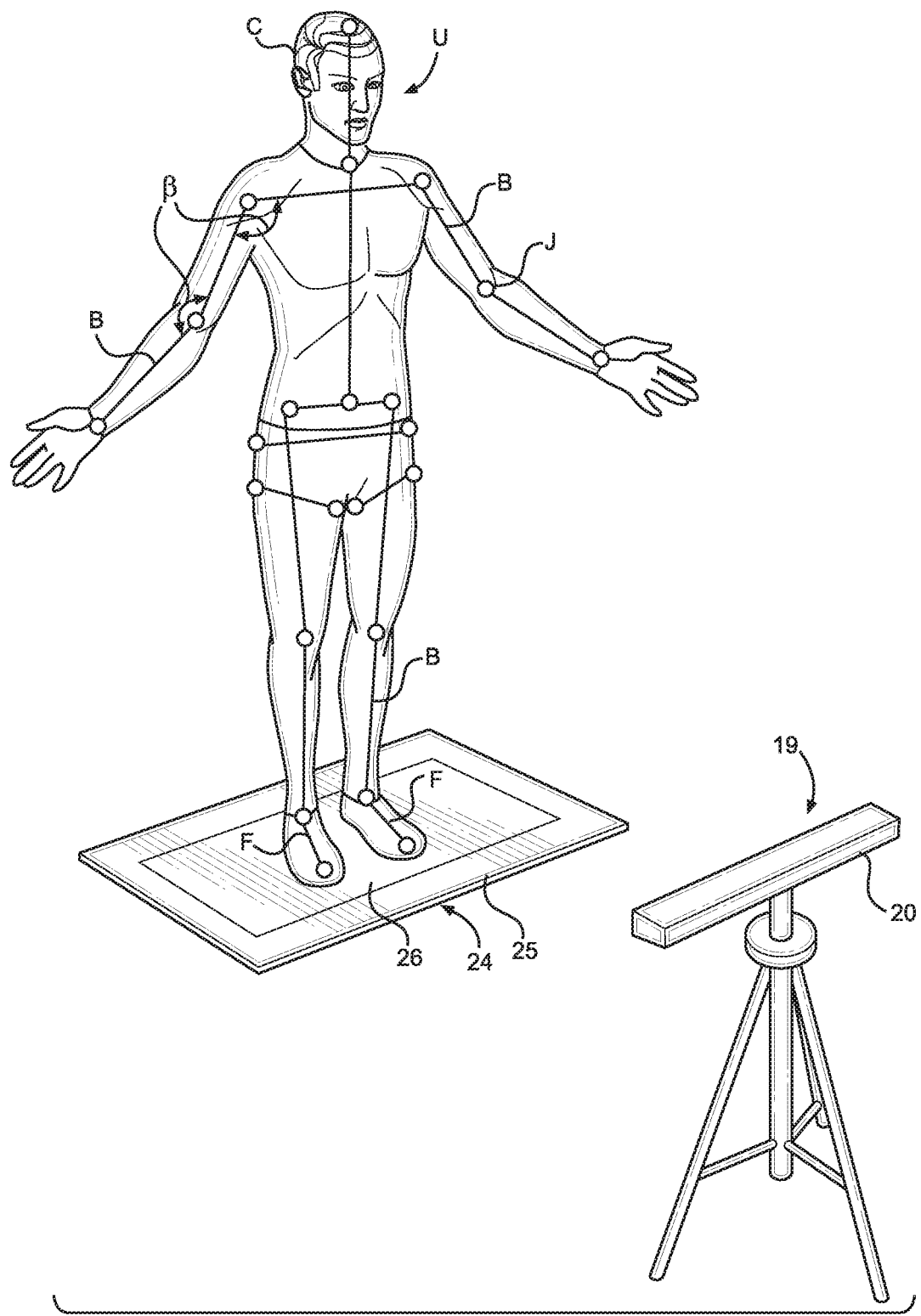
FIG. 4 is a schematic perspective view of a user in a standing position in front of a second detail of the system of FIG. 1.
Figure 5:
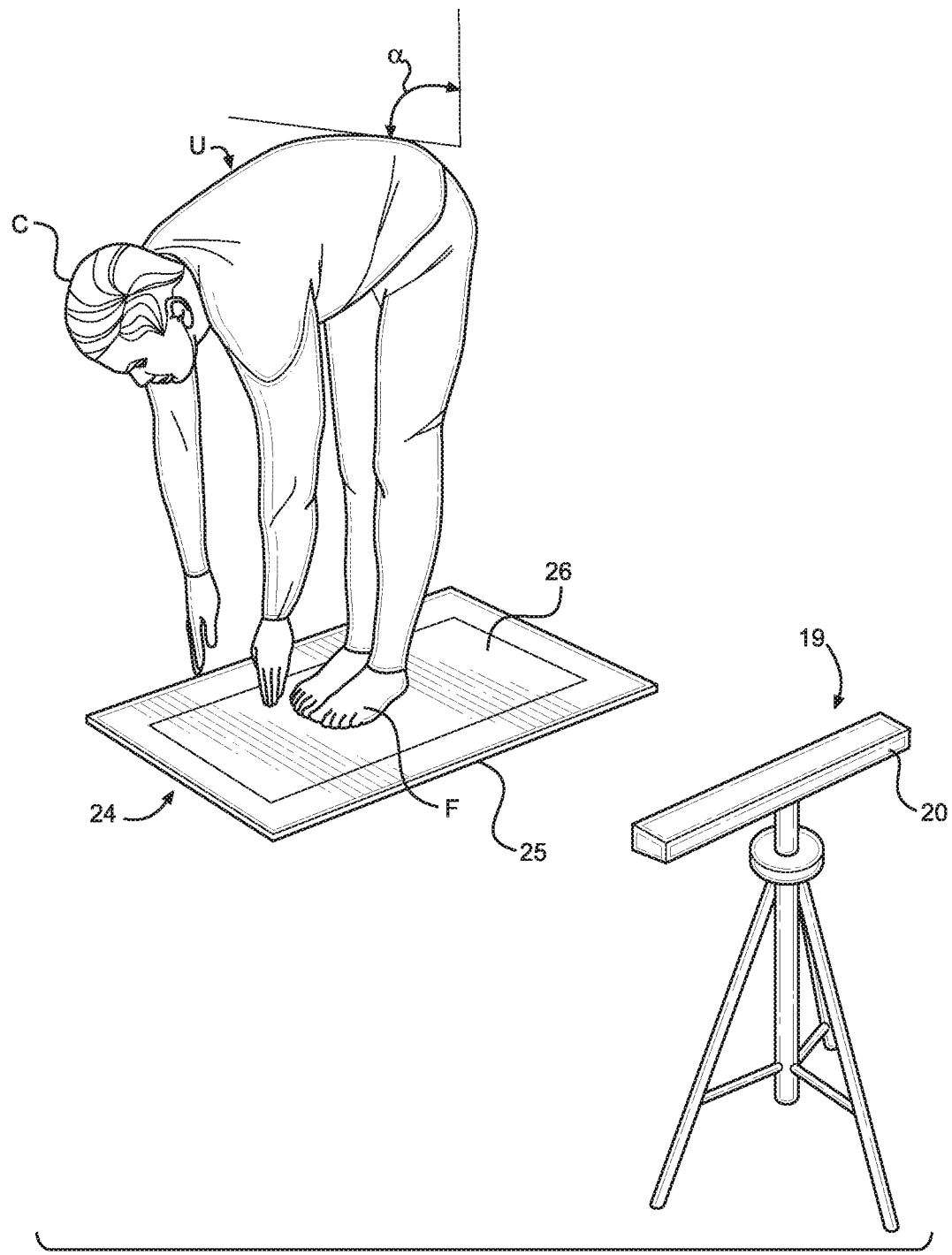
FIG. 5 is a schematic perspective view of a user in a bent position in front of a second detail of the system of FIG. 1.
Figure 6:
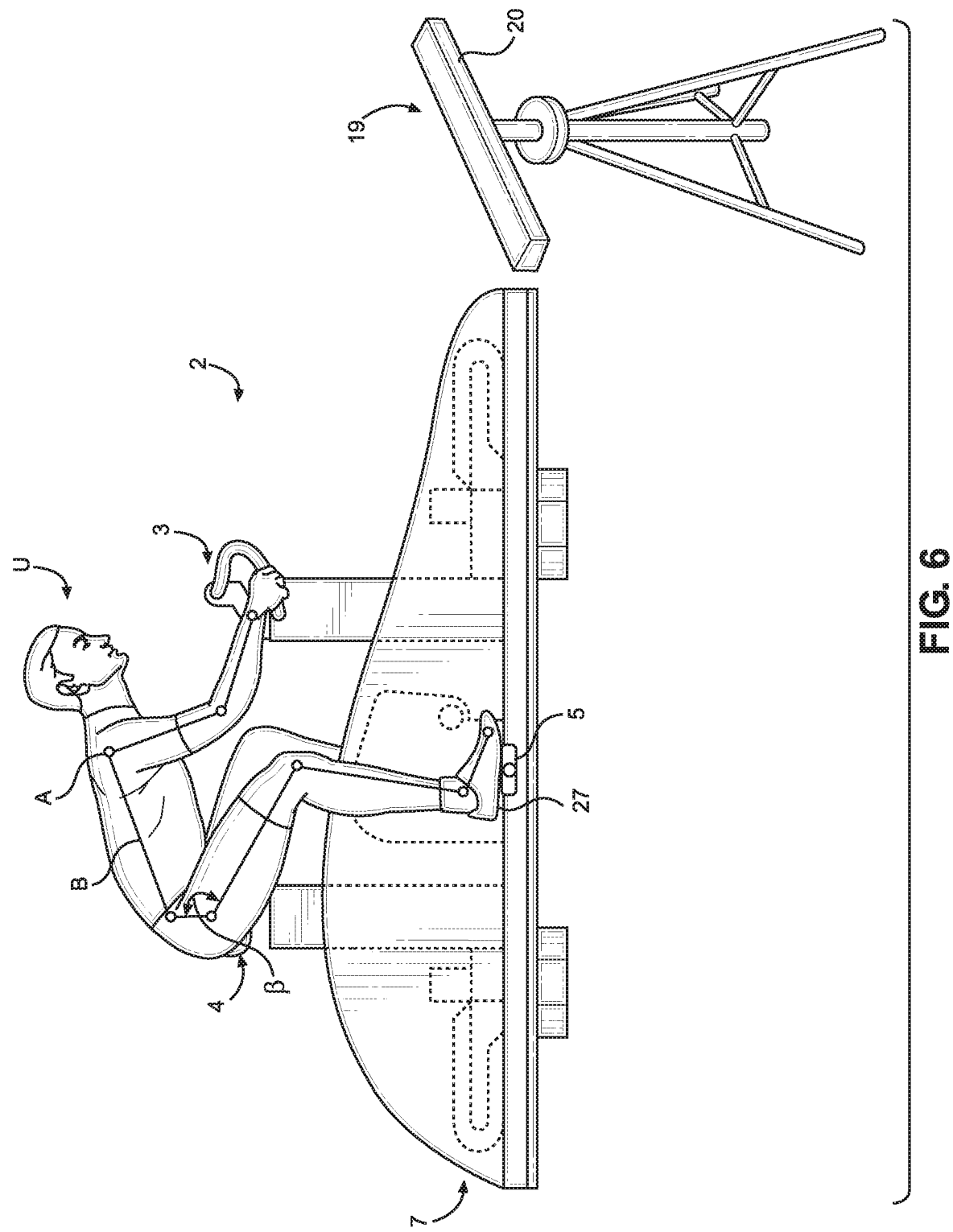
FIG. 6 is a schematic perspective view of a user in front of a second detail of the system of FIG. 1 during the pedaling action.

These physical data units $D_F$ are acquired with the user U in a stationary standing position, as shown in FIG. 4, in a bent position, as shown in FIG. 5, or during a pedaling test on the simulator 2, as shown in FIG. 6.

The system also comprises a pressure sensor assembly 24 including an electronic platform 25, as shown in FIGS. 1, 2, 4 e 5, for detecting pressure data $D_W$ associated with the feet F of the user U either in a stationary standing position, as shown in FIG. 4 or in a belt position, as shown in FIG. 5.

For this purpose, the platform 25 incorporates a first set of sensors 26, preferably an array of capacitive sensors for sensing the pressure exerted by the feet F of the user U when the latter is in a stationary standing position or a forward bend position.

Figure 7:
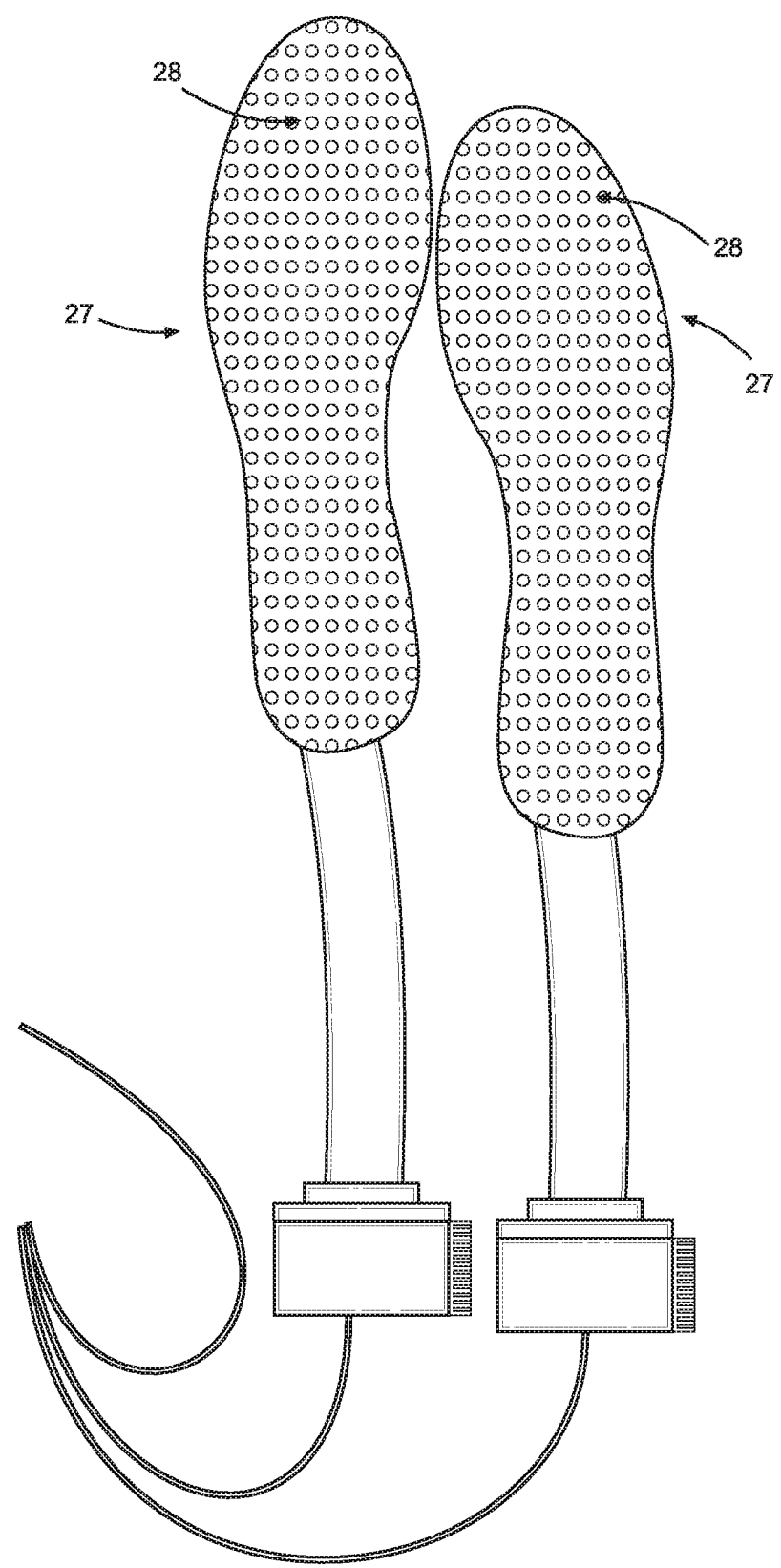
FIG. 7 is a top view of a fourth detail of the system of FIG. 2.

The assembly 24 further comprises a pair of insoles 27, as shown in FIG. 7, to be introduced into the shoes S of the user U for detecting the pressure exerted by the latter in the plantar region during pedaling.

Preferably, each insole 27 may incorporate therein a second set of sensors 28 for sensing the pressure exerted by the user in the plantar region during pedaling and transmitting relevant pressure data to the computer 14.

The pressure sensor assembly 24 may comprise a third set of sensors 29 associated with the handlebar 3 and the saddle 4 of the simulator 2 for sensing the pressure exerted by the user U at the hands M and the buttocks G during pedaling.

Software SW may be installed on the computer 14 for processing historical data $D_A$, physical data $D_F$ and pressure data $D_W$ as sensed on the user U in stationary standing and bent positions, to select corresponding optimal angular ranges $\beta_{REF}$ from those previously stored in the memory unit 16.

The selected initial optimized data $D_{IN}$ may be thus compared with the instantaneous data $D_{IS}$ of the user U as detected by the 3D scanner 20 during pedaling to generate final data $D_{OUT}$ of the optimized shape and position characteristics of the main parts of the bicycle.

Furthermore, the software SW may be adapted to process the final data $D_{OUT}$ using an appropriate algorithm A within the software SW to represent the final data $D_{OUT}$ by spatial representation means 30 and control the actuation of the actuators 6 of the simulator 2.

Particularly, the computer 14 will be adapted to generate respective control signals $S_C$, which may vary according to the final data $D_{OUT}$ to promote vertical displacement y of the handlebar 3 and/or vertical y' and horizontal x displacements of the saddle 4 while the user U is pedaling.

Figure 8:
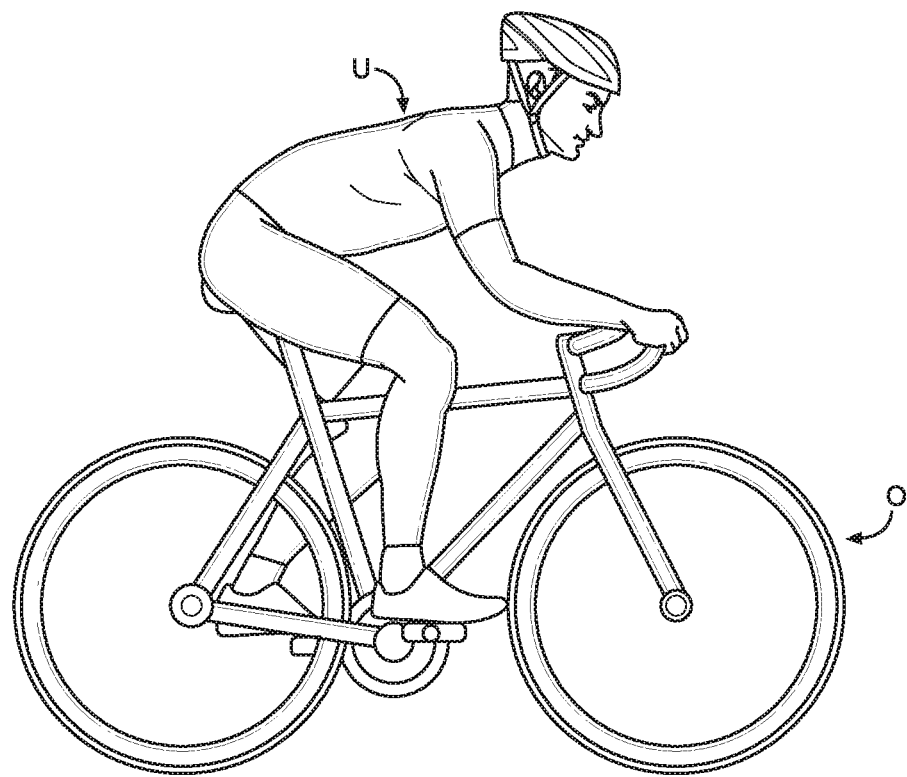
FIG. 8 is a front perspective view of a fifth detail of FIG. 2.
Figure 8:
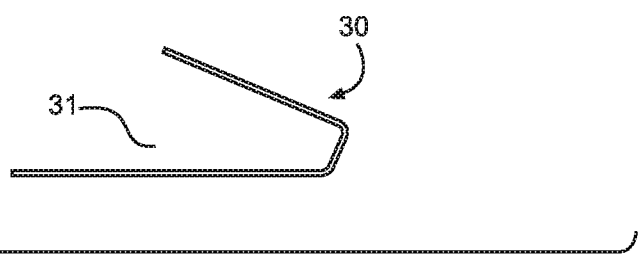

As shown in FIG. 8, the representation means 30 may be adapted to spatially represent the final data $D_{OUT}$ in the form of a holographic image O of the user U on the bicycle for any checking and/or correction purpose.

Preferably, the spatial representation means 30 may comprise a 3D holographic projector 31.

The system 1 may further comprise instantaneous manufacturing means 32 for instantaneously manufacturing optimized parts and/or means for selecting bicycle parts corresponding to previously manufactured optimized parts, in stock in warehouses or stored, not shown.

Preferably, the instantaneous manufacturing means 32 may comprise one or more 3D printers, not shown and known per se, which are connected to the computer 14 and are adapted to process the final data $D_{OUT}$ for real-time spatial printing of an optimized part.

Figure 9:
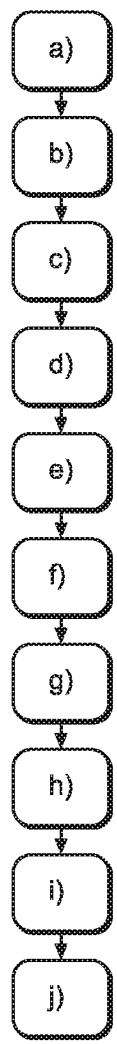
FIG. 9 is a block diagram of a method of biomechanical analysis of the posture of a user according to the invention.

The block diagram of FIG. 9 schematically shows a method of biomechanical analysis of the posture of a user U, using at least all the components of the above-described system.

The method includes a first step of a) determining a matrix of optimal angular ranges $\beta_{REF}$ between body segments B of a general user U at his/her joints J.

The matrix of optimal angular ranges $\beta_{REF}$ between the body segments B of the user U may be constructed according to the cycling discipline and its difficulty level.

A second step is then carried out, i.e. b) collecting historical data $D_A$ of the user U and converting it into numeric strings for use by a computer 14, followed by a third step of c) functional morphological analysis of the user U by detection of the body segments B of the user U by means of the scanner 20 to obtain corresponding anthropometric data $D_L$ associated with the user.

The morphological analysis step c) by the scanner 20 may also include optometric scanning of the perimeter of the feet F of the user U for automatic detection of the main axes and lengths thereof.

A step is also included of d) analyzing any dysmetria or postural defect of the user U by detecting corresponding pressure data $D_W$ at the feet F of the user U when the latter is in either standing or forward bend stationary position. Particularly, this analysis may include measurement of the sacral plane a in the forward bent position, according to the Adams' test.

Particularly, this analysis step d) may be carried out by placing the user U on the capacitive platform 25 as described above and shown in FIGS. 4 and 5.

The method further includes a step of e) providing a computer 14 with software SW installed therein for processing the optimal angular ranges $\beta_{REF}$ stored in the memory unit 16 thereof, the numeric strings of historical data $D_A$ and the pressure data $D_W$ to determine initial data $D_{IN}$ associated with the user U and corresponding to the main parts of the bicycle.

For instance, the initial data may be associated with the shapes and sizes of the handlebar 3 and the frame 7, or the type of saddle 4 suitable for the user U.

The next step comprises f) providing a simulator 2 assisted by the computer 14, as described above, having sensors 29 in the saddle 4 and the handlebar 3 and actuators 6 for automatically changing the optimized three-dimensional position of the saddle 4 and the handlebar 3 according to the initial data $D_{IN}$.

In the next step g) the user U gets onto the simulator 2 and undergoes a dynamic test with a standard pedaling resistance to obtain instantaneous data $D_{IS}$, in addition to the detection of pressure data $D_W$ and of the instantaneous angles $\beta$ between body segments B by the scanner 20 during pedaling.

The pressure data $D_W$ may be sensed by the sensors 28 incorporated in the insoles 27 within the shoes S worn by the user U during the dynamic pedaling test, as well as by the sensors 29 mounted to the handlebar 3 and the saddle 4.

As the user U is pedaling, he/she may be assisted by instructions on a digital display mounted to the simulator 2 and not shown in the figures, to monitor the pedaling conditions and the position of the body segments B as detected by the 3S scanner 20.

Then, during step h), the instantaneous data $D_{IS}$ is compared with the initial data $D_{IN}$ by the computer 14 to obtain the optimized final data $D_{OUT}$ of the bicycle to be transmitted to the simulator 2.

Thus, the position of the saddle 4 and the handlebar 3 will be automatically changed to fit the shape and the size of the frame 3 and the pedal cranks 5.

In order to check proper positioning of the user U and make any final corrections, there is provided a step i) of holographic representation of the image O of the user U and the optimized configuration of the bicycle on the simulator 2 by a holographic projector 31 controlled by the computer 14.

During this three-dimensional projection step i), the image O of the user may be rotated and moved using any electronic pointer, possibly a sensor or virtual pointer, which is not shown as being known per se, to check the optimal configuration from every side.

Finally, the method includes a step of j) transmitting the optimized final data $D_{OUT}$ to one or more 3D printers, not shown, to manufacture the basic parts of the bicycle, such as the saddle, the handlebar, the frame and the pedal cranks.

An alternative thereto may be computerized selection of existing parts in stock in warehouses or stores, from predetermined databases.

The system and method as described above have proven that the time for biomechanical analyses and preparation of the various parts of the customized bicycle is dramatically reduced from hours to a few minutes, indicatively about 20 minutes, which affords a considerable advantage for operators.

The system and method of the invention are susceptible to a number of changes or variants, within the inventive concept disclosed in the annexed claims. All the details thereof may be replaced by other technically equivalent parts, and the materials may vary depending on different needs, without departure from the scope of the invention.

While the system and method have been described with particular reference to the accompanying figures, the numerals referred to in the disclosure and claims are only used for the sake of a better intelligibility of the invention and shall not be intended to limit the claimed scope in any manner.

The invention claimed is:

1. A method of biomechanical analysis of a posture of a user, and of automatic customized manufacture of bicycle parts, comprising the steps of:
    a) determining a matrix of optimal angular ranges ($\beta_{REF}$) between body segments (B) of a user (U) at his/her joints (J);
    b) collecting historical data ($D_A$) of the user (U) and converting the historical data into numeric strings;
    c) performing a functional morphological analysis of the user (U) by detecting positions of the body segments (B) of the user (U) with a 3D scanner (20);
    d) analyzing dysmetria and postural defects of the user (U) using pressure data ($D_W$) detected in standing and bent positions by a platform (25);
    e) providing a computer (14) with software (SW) installed therein for processing said optimal angular ranges ($\beta_{REF}$), said numeric strings of the historical data ($D_A$), and said pressure data ($D_W$) to determine initial data ($D_{IN}$) concerning parts of a bicycle;
    f) providing pressure sensors (28) associated with insoles (27) designed to be inserted into shoes (S) of the user (U) and a servo-assisted pedaling simulator (2) assisted by said computer (14), having additional pressure sensors (29) in saddle (4) and handlebar (3) and actuators (6) for automatically changing an optimized three-dimensional position of the saddle (4) and the handlebar (3) according to said initial data ($D_{IN}$);
    g) detecting the pressure data ($D_W$) at a specific moment using said sensors (28, 29) and angles ($\beta$) between body segments (B) using said 3D scanner (20) during a dynamic test of the user (U) on said servo-assisted pedaling simulator (2) by setting a standard pedaling resistance thereon, according to heartbeat rate, to obtain instantaneous data ($D_{IS}$);
    h) comparing said instantaneous data ($D_{IS}$) with said initial data ($D_{IN}$) by said computer (14) to obtain optimized final data ($D_{OUT}$) of the bicycle, to be transmitted to said servo-assisted pedaling simulator (2) for automatic adaptation of a position of the saddle (4) and for configuration of shapes and sizes of frame (7) and pedal cranks (5);
    i) providing a holographic spatial representation of an image (0) of the user (U) on the servo-assisted pedaling simulator (2) and an optimized configuration of the bicycle by a 3D holographic projector (31) controlled by said computer (14), to check proper positioning of the user (U) and make any corrections to configuration; and
    j) transmitting said optimized final data ($D_{OUT}$) to one or more 3D printers for instantaneous manufacture of the parts of the bicycle using this three-dimensional technology or, alternatively, for computerized selection of existing parts in stock in warehouses and stores from databases.

2. The method as claimed in claim 1, wherein said matrix of optimal angular ranges ($\beta_{REF}$) of the user (U) is determined according to cycling discipline and difficulty level selected by the user (U).

3. The method as claimed in claim 1, wherein, before said dynamic test, the user (U) undergoes an analysis of sacral plane inclination ($\alpha$) in a forward bent position according to Adams' test.

4. The method as claimed in claim 1, wherein, during the step of performing the functional morphological analysis, optometric scanning of perimeter of the user's feet (F) is performed for automatic detection of main axes and main dimensions thereof.

5. The method as claimed in claim 1, wherein, during the dynamic test, the user (U) follows instructions on a digital display mounted to the servo-assisted pedaling simulator (2) to monitor pedaling conditions and position of the body segments (B) as detected by said 3D scanner (20).

6. The method as claimed in claim 1, wherein, during the step i) of providing the holographic representation of the user (U), the image (0) is rotated and moved to check optimal configuration from every side.

7. A system for biomechanical analysis of a posture of a user (U) and for automatic customized manufacture of parts of a bicycle, for carrying out the method as claimed in claim 1, comprising:
    the servo-assisted pedaling simulator (2) having at least one handlebar (3), a saddle (4), a pair of pedal cranks (5), and a plurality of actuators (6) for changing position of the handlebar (3) and the saddle (4);
    a detection device (19) acquiring anthropometric input data ($D_L$) of a user (U), wherein said detection device (19) comprises:
    the 3D scanner (20) automatically detecting the positions of the body segments (B) of the user (U) and the angles ($\beta$) therebetween, and generating a plurality of three-dimensional physical data units ($D_F$) of the user (U);
    a pressure sensor assembly (24) detecting pressure data ($D_W$) of the user (U);
    the computer (14) associated with said servo-assisted pedaling simulator (2), having an interface (15) and operably connected with said actuators (6) and said detection device (19);
    a memory unit (16) associated with said computer (14) for storing optimized initial data ($D_{IN}$) and instantaneous data ($D_{IS}$) of the user (U); and
    the software (SW) installed on said computer (14) comparing said optimized initial data ($D_{IN}$) and said instantaneous data ($D_{IS}$) of the user (U) and generating final data ($D_{OUT}$) of an optimized shape and position characteristics of main parts of a bicycle using an algorithm (A) controlling actuation of said actuators (6);
    wherein said pressure sensor assembly (24) comprises:

at last one electronic platform (25) detecting the pressure data ($D_W$) of the user (U) in a stationary standing or forward bent position, and the insoles (27) designed to be inserted into shoes (S) of the user (U) for detecting a pressure exerted by the user (U) in a plantar region during pedaling, and wherein a spatial representation system (30) is provided spatially representing said final data ($D_{OUT}$) as a 3D hologram (O) of the user (U) during pedaling for checking and possibly correction purposes.

8. The system as claimed in claim 7, wherein said platform (25) incorporates a first set of sensors (26), sensing pressure exerted by feet (F) of the user (U) when the user is in a stationary standing or forward bent position.

9. The system as claimed in claim 7, wherein each insole (27) incorporates therein a second set of sensors (28) sensing a pressure exerted by the user (U) in a plantar region during pedaling.

10. The system as claimed in claim 7, wherein said handlebar (3) and said saddle (4) of the servo-assisted pedaling simulator (2) incorporate therein a third set of sensors (29) for sensing a pressure exerted by the user (U) at hands (M) and buttocks (G) during pedaling.

11. The system as claimed in claim 7, wherein said 3D scanner (20) comprises a processor (23) processing a scanned image of the user (U) and determining shapes and positions of the body segments (B) of the user, coupled at the user's joints (J), to measure the angles ($\beta$) therebetween.

12. The system as claimed in claim 7, wherein said spatial representation system (30) spatially representing said final data ($D_{OUT}$) comprise the 3D holographic projector (31).

13. The system as claimed in claim 7, further comprising a system for instantaneous manufacture (32) of optimized parts, the system for the instantaneous manufacture (32) processing the final data ($D_{OUT}$) for the instantaneous manufacture of the optimized parts.

14. The system as claimed in claim 13, wherein said system (32) for instantaneous manufacture of said optimized parts comprise the one or more 3D printers.

* * * * *